United States Patent
Johnson et al.

(10) Patent No.: US 12,254,992 B2
(45) Date of Patent: Mar. 18, 2025

(54) CONTACT TRACING UTILIZING DEVICE SIGNATURES CAPTURED DURING TRANSACTIONS

(71) Applicant: International Business Machines Corporation, Armonk, NY (US)

(72) Inventors: Richard C. Johnson, Selkirk, NY (US); Alex Richard Hubbard, Rensselaer, NY (US); Cody J. Murray, Burnt Hills, NY (US); Vinay Pai, Albany, NY (US); Nikhil Jain, Albany, NY (US)

(73) Assignee: International Business Machines Corporation, Armonk, NY (US)

( * ) Notice: Subject to any disclaimer, the term of this patent is extended or adjusted under 35 U.S.C. 154(b) by 225 days.

(21) Appl. No.: 17/356,796

(22) Filed: Jun. 24, 2021

(65) Prior Publication Data
US 2022/0415523 A1    Dec. 29, 2022

(51) Int. Cl.
*G16H 50/80*   (2018.01)
*G06Q 20/20*   (2012.01)

(52) U.S. Cl.
CPC ............. *G16H 50/80* (2018.01); *G06Q 20/20* (2013.01)

(58) Field of Classification Search
None
See application file for complete search history.

(56) References Cited

U.S. PATENT DOCUMENTS

| | | | |
|---|---|---|---|
| 10,216,917 B2 | 2/2019 | Johnson | |
| 10,251,610 B2* | 4/2019 | Parthasarathy | A61B 5/01 |
| 10,984,496 B1* | 4/2021 | Rabb | A61B 6/5294 |
| 2014/0095417 A1* | 4/2014 | Herz | G16H 50/80 |
| | | | 706/12 |
| 2015/0051953 A1* | 2/2015 | Howe | G06Q 30/0205 |
| | | | 705/7.34 |
| 2015/0081446 A1* | 3/2015 | Callahan | G06Q 30/08 |
| | | | 705/28 |
| 2016/0071115 A1* | 3/2016 | Oh | G06Q 20/202 |
| | | | 705/7.29 |
| 2016/0110702 A1* | 4/2016 | Landers, Jr. | G07G 1/0054 |
| | | | 705/17 |
| 2016/0140311 A1 | 5/2016 | Pastore | |
| 2016/0342770 A1 | 11/2016 | Unser | |

(Continued)

FOREIGN PATENT DOCUMENTS

| | | | | |
|---|---|---|---|---|
| KR | 20220048502 A | * | 10/2020 | G16H 50/80 |
| WO | WO-2013116894 A1 | * | 8/2013 | G06Q 30/02 |

OTHER PUBLICATIONS

Pax Technology Blog, Jul. 15, 2020, "PAX and Smart Volution enable COVID-19 contact tracing for in-store customers using Android payment terminals" with Facebook Press Release announcement for article dated Jul. 16, 2020 (Year: 2020).*

(Continued)

*Primary Examiner* — Anne-Marie K Alderson
(74) *Attorney, Agent, or Firm* — Edward J. Wixted, III

(57) ABSTRACT

In an approach, a processor receives device identification information corresponding to at least one device local to a location of a transaction. A processor receives notification of an infected user. A processor determines that the infected user is associated with the transaction. A processor identifies a second user from the device identification information. A processor sends a notification to the second user.

15 Claims, 4 Drawing Sheets

(56) References Cited

U.S. PATENT DOCUMENTS

| | | | | |
|---|---|---|---|---|
| 2017/0034668 A1* | 2/2017 | Berentsen | | H04W 4/33 |
| 2017/0243188 A1* | 8/2017 | Mahmoudzadehvazifeh | | |
| | | | | G06Q 20/202 |
| 2017/0352119 A1* | 12/2017 | Pittman | | G16H 50/80 |
| 2019/0312883 A1* | 10/2019 | McCarter | | H04L 9/088 |
| 2020/0234297 A1 | 7/2020 | Murray | | |
| 2021/0365445 A1* | 11/2021 | Robell | | G06F 16/90 |
| 2022/0122741 A1* | 4/2022 | Mody | | H04W 12/088 |

OTHER PUBLICATIONS

Pax Technology blog, "contact tracing for in-store customers using Android payment terminals", published on www.paxtechnology.com/blog/ Jul. 15, 2020 (Year: 2020).*

"A Method and Apparatus for Consumer Data Association", An IP.com Prior Art Database Technical Disclosure, IP.com No. IPCOM000244024D, Nov. 5, 2015, 3 pages.

* cited by examiner

CONTACT TRACING UTILIZING DEVICE SIGNATURES CAPTURED DURING TRANSACTIONS

BACKGROUND

The present invention relates generally to the field of contact tracing, and more particularly to contact tracing using device information captured by a point-of-service (POS) device during a transaction.

Contact tracing is the process of identifying persons who may have come into contact with an infected person and subsequent collection of further information about these contacts. By tracing the contacts of infected individuals, testing them for infections, isolating/treating the infected, and tracing their contacts, infection rates in the population can be reduced. Some goals of contact tracing are to interrupt ongoing transmission and reduce the spread of an infection, to alert contacts to the possibility of infection and offer preventative services or care, to offer diagnosis/treatment to already infected individuals.

SUMMARY

According to one embodiment of the present invention, a computer-implemented method, computer program product, and computer system are provided. A processor receives device identification information corresponding to at least one device local to a location of a transaction. A processor receives notification of an infected user. A processor determines that the infected user is associated with the transaction. A processor identifies a second user from the device identification information. A processor sends a notification to the second user.

DETAILED DESCRIPTION

Embodiments of the present invention recognize that current automated methods of contact tracing rely on, for example, phone location data that is collected by phone carriers of users who have enabled location-services and opted in to a contact tracing service. Embodiments of the present invention further recognize that, as location data is required, areas that have poor cellular reception or poor access to global positioning signal (GPS) services may result in poor performance of current contact tracing approaches.

Embodiments of the present invention provide an approach to utilize point-of-sale (POS) devices, that are capable of scanning local devices, to detect media access control (MAC) addresses of nearby devices when a transaction is made and send such MAC address information to the financial institution associated with the transaction. Upon an institution (e.g., Centers for Disease Control and Prevention (CDC) or other public health organization) receiving a MAC address(es) associated with an individual that has been identified as infected with a disease, the institution can query financial institution(s) to identify transactions containing the MAC address(es) associated with the individual and may identify other devices that are included in those transactions as belonging to individuals who may have come in contact with the infected individual such that such individuals may be contacted. Embodiments of the present invention recognize that, by using a POS device to detect nearby devices, contact tracing services may be able to be provided even in locations with poor access to cellular or GPS networks.

The present invention will now be described in detail with reference to the Figures.

Figure 1:
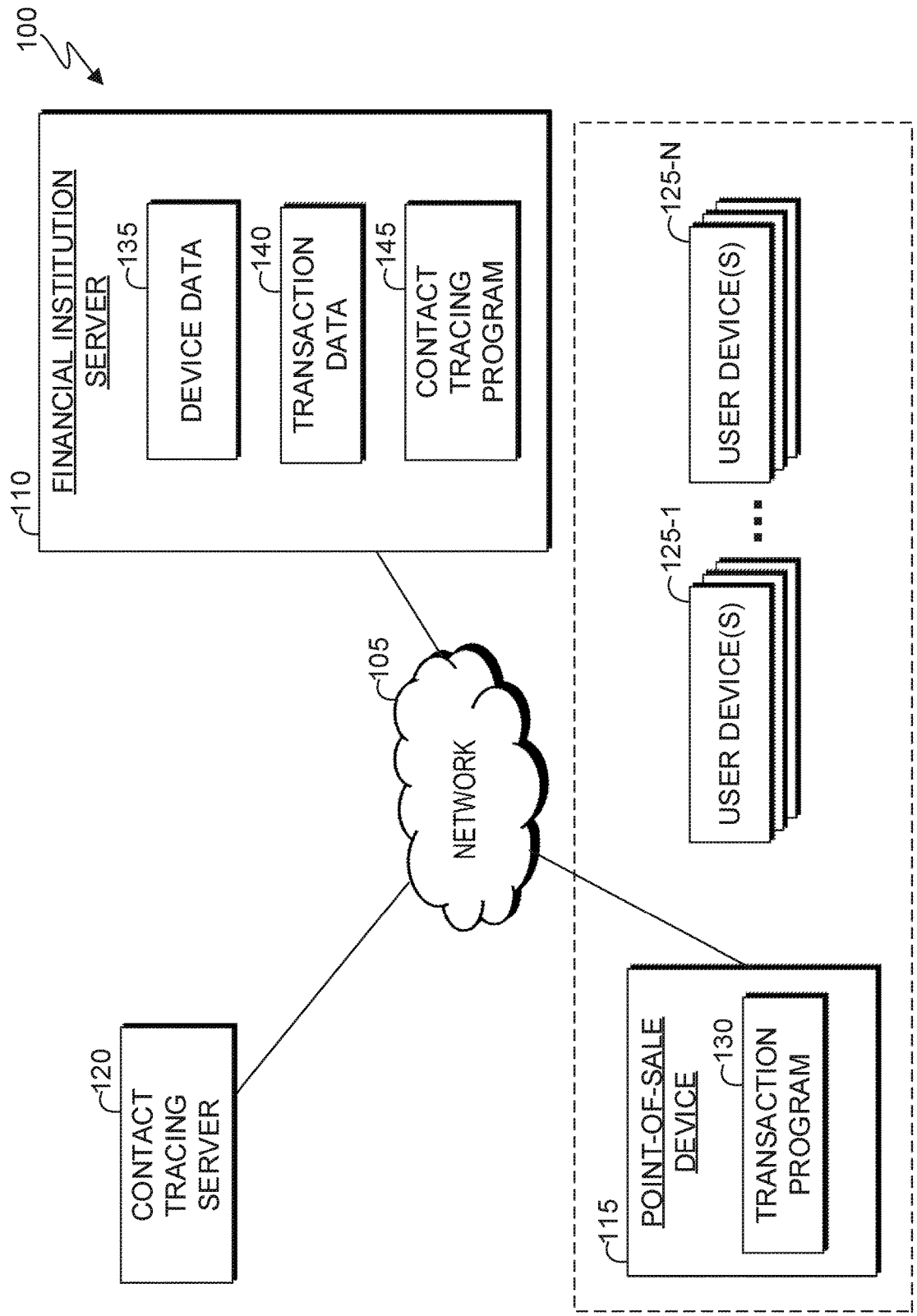
FIG. 1 is a functional block diagram illustrating a computer environment, in accordance with an embodiment of the present invention.

FIG. 1 is a functional block diagram illustrating a computing environment, generally designated 100, in accordance with one embodiment of the present invention. FIG. 1 provides only an illustration of one embodiment and does not imply any limitations with regards to the environments in which different embodiments may be implemented.

In the depicted embodiment, computing environment 100 includes financial institution server 110, POS device 115, and contact tracing server 120 interconnected over network 105. Network 105 may be a local area network (LAN), a wide area network (WAN), such as the Internet, the public switched telephone network (PSTN), any combination thereof, or any combination of connections and protocols that will support communications between financial institution server 110, POS device 115, and contact tracing server 120, in accordance with embodiments of the present invention. Network 105 may include wired, wireless, or fiber optic connections. Computing environment 100 also includes user device(s) 125-1 through 125-N which are geographically located near (e.g., within a threshold distance of) POS device 115, such that POS device 115 is able to identify the presence of user device(s) 125-1 through 125-N. The dotted line surrounding POS device 115 and user device(s) 125-1 through 125-N is a visual representation of the devices being located within a particular geographic location. Computing environment 100 may include additional servers, computing devices, or other devices not shown.

POS device 115 may be, for example, a cash register, automated ordering kiosk, tablet, computing device, or any other electronic device capable of sending and receiving data and communicating with financial institution server 110 via network 105. POS device 115 is generally a device that facilitates POS transactions, such as credit/debit card transactions using either physical cards or digital wallets. POS device 115 verifies credit card information (e.g., routing numbers, account numbers, the identity of the owner of the credit card). POS device 115 includes radio wave signal device(s) and is capable of the radio wave signal device(s) to generate and/receive one or more radio wave signals (e.g., Wi-Fi®, Bluetooth®, Bluetooth® Low Energy, near-field communication (NFC)) to search for devices, such as user device(s) 125-1 through 125-N that geographically near POS device 115. As used herein, a user device 125 being geographically near POS device 115 refers to the user device 125 being within range of the type of radio wave signal used by POS device 115, such that POS device 115 is able to identify the presence of the user device 125. In some embodiments, the area covered by the radio wave signal of POS device 115 is a radius (e.g., inches, feet, yards) around POS device 115. POS device 115 contains transaction program 130. POS device 115 may include components, as depicted and described in further detail with respect to FIG. 4.

Devices 125-1 through 125-N may represent any number of electronic devices that include information identifiable by POS device 115. Devices 125 may include, for example, smartphones, smartwatches, tablets, laptops, fitness trackers, or any other Internet of things (IoT) device or other device that generates a unique identifier accessible by POS device 115, such as a media access control (MAC) address. As depicted in FIG. 1, user device(s) 125-1 are devices associated with a first user and user device(s) 125-N are devices of an Nth user. Each user may have different types and numbers of user device(s) 125. Each user device 125 may have a unique identifier such as, for example a (MAC) address. Users may store device 125 information to a library (e.g., device data 135) associated with their particular credit/debit account such that financial institution server 110 has access to the library. The library therefore may identify that a particular user device 125 belongs to a particular user associated with a particular credit/debit card and account. Devices 125-1 through 125-N may each include components, as depicted and described in further detail with respect to FIG. 4.

Transaction program 130 operates to provide retail services and process transaction requests, identify devices that are identifiable by POS device 115, and send the transaction details and monitored device information to financial institution server 110. In one embodiment, transaction program 130 resides on POS device 115. In other embodiments, transaction program 130 may reside on another computing device or server, provided that transaction program 130 has access to POS device 115 and financial institution server 110, transaction data 140, and/or device data 135. In some embodiments, transaction program 130 is integrated with a particular set of retail services. In other embodiments, transaction program 130 is an external application that may operate with multiple retail services. In such embodiments, transaction program 130 may be an external application implemented as a microservice or module that facilitates the collection of user device 125 information that is located geographically near POS device 115 at, or around (e.g., within a predefined time period, specified by an administrative user, before or after the transaction), the time of a particular transaction. In some embodiments, various retailers and/or financial institutions may implement the services provided by transaction program 130 to allow the system to operate across multiple retailers and with multiple financial institutions. In such an embodiment, a user may create an account with such a service provider and cause their device information and account information to be stored to a library, as previously described. At any time, users may grant or restrict what data is used and how that data is used and/or shared.

Contact tracing server 120 may be a management server, a web server, or any other electronic device or computing system capable of sending and receiving data and communicating with financial institution server 110 and user device(s) 125-1 through 125-N. In some embodiments, contact tracing server 120 may represent a server computing system utilizing multiple computers as a server system, such as in a cloud computing environment. Contact tracing server 120 may be an enterprise server capable of facilitating contact tracing services provided by, for example, a public health institution. Contact tracing server 120 may include components, as depicted and described in further detail with respect to FIG. 4.

Financial institution server 110 may be a management server, a web server, or any other electronic device or computing system capable of sending and receiving data and communicating with contact tracing server 120 and POS device 115 via network 105. In some embodiments, financial institution server 110 may represent a server computing system utilizing multiple computers as a server system, such as in a cloud computing environment. Financial institution server 110 may be an enterprise server capable of facilitating transactional services, such as services provided by a bank or credit card institution. Financial institution server 110 contains device data 135, transaction data 140, and contact tracing program 145. Financial institution server 110 may include components, as depicted and described in further detail with respect to FIG. 4.

Device data 135 is a repository that contains device information corresponding to user accounts associated with, for example, credit/debit accounts. As described above, a user my cause one or more user device(s) 125 to be associated with the user and the user's account. Such information is then stored to device data repository 135 for access by contact tracing program 145 and/or transaction program 130. In one embodiment, device data 135 resides on financial institution server 110. In other embodiments, device data 135 may reside on another server or another computing device, provided that device data is accessible to contact tracing program 145 and/or transaction program 130.

Transaction data 140 is a repository that contains transaction data and user device 125 data associated with a particular transaction. As previously described, POS device 115 may identify user devices 125 geographically near POS device 115 at, or around, the time a transaction is made by a user. Each transaction stored to transaction data 140 may include the transaction details (e.g., routing numbers, account numbers, the identity of the owner of the credit card, items purchased, money transferred) as well as identified user devices 125. Such information is stored to transaction data 140 for access by contact tracing program 145 and/or transaction program 130. In one embodiment, transaction data 140 resides on financial institution server 110. In other embodiments, transaction data 140 may reside on another server or another computing device, provided that device data is accessible to contact tracing program 145 and/or transaction program 130.

Contact tracing program 145 operates to receive a notification of a user with an infection (e.g., infectious disease) from a contact tracing institution such that contact tracing program 145 can associate user device 125 information that was geographically near POS device 115 at any time(s) the infected user generated transactions. Contact tracing program 145 compares transaction data 140 to device data 135 and identifies one or more user device(s) 125. Contacting tracing program 140 may then notify, or cause contact tracing server 120 to notify, the users associated with the one or more user device(s) 125 that they may have been exposed to the possible infection. In one embodiment, contact tracing program 145 resides on financial institution server 140. In other embodiments, contact tracing program 145 may reside on contact tracing server 120, and other server, or another computing device, provided that contact tracing program 145 has access to transaction data 140 and device data 135, and provided that contact tracing program is able to send notifications to user device(s) 125-1 through 125-N.

Figure 2:
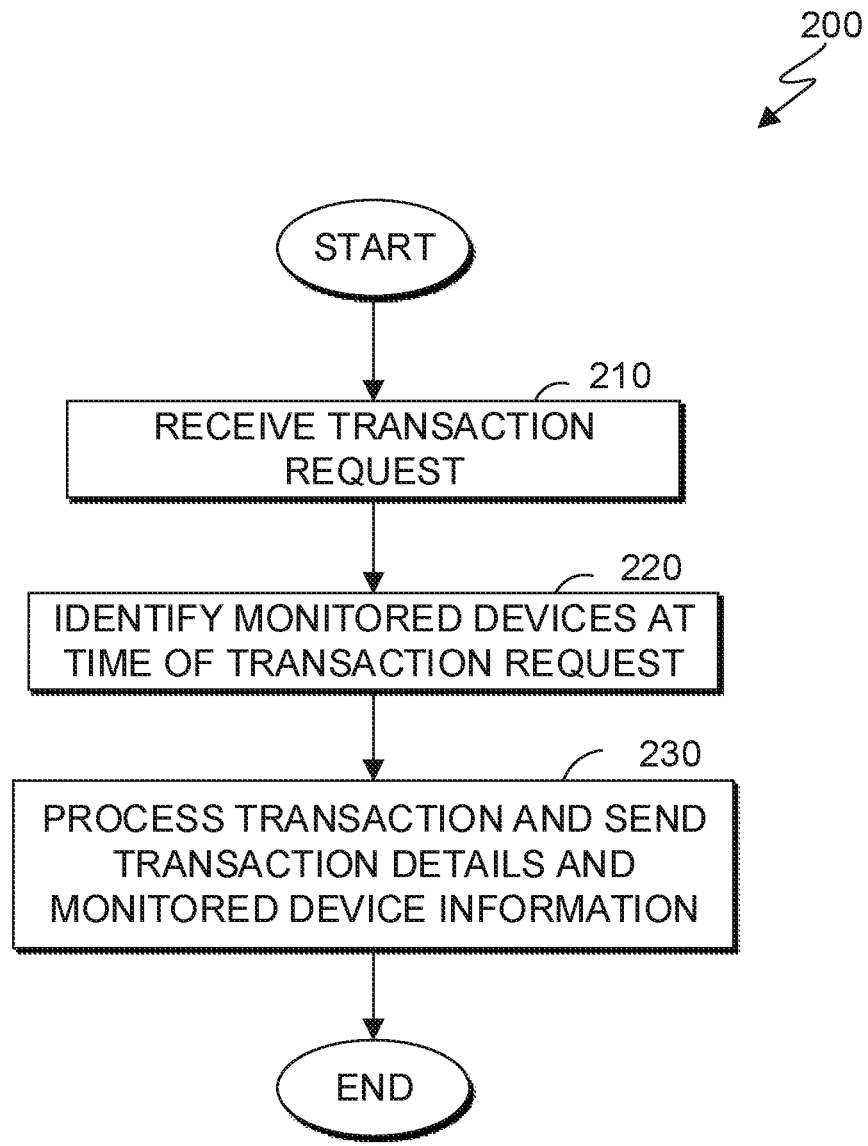
FIG. 2 is a flowchart depicting operational steps of a transaction program executing within the computer environment of FIG. 1, for processing transactions and identifying devices located near the transactions, in accordance with an embodiment of the present invention.

FIG. 2 depicts a flowchart 200 for the steps of transaction program 130, executing within computing environment 100 of FIG. 1, for processing a POS transaction and identifying user devices 125 located geographically near POS device 115 at or around the time of the transaction.

In step 210, transaction program 130 receives a transaction request. The transaction request may be, for example, a credit/debit card transaction to purchase goods/services performed at a retail establishment. Transaction program 130 may receive the transaction request as a result of a card swipe, card chip read, bar code scan, NFC read, or other means of initiating payment to process a transaction performed by a user, such as a user of user device(s) 125-1. For example, a user may place a smartphone type of user device 125 near POS device 115 and an NFC transaction may begin.

In step 220, transaction program 130 identifies monitored user devices 125 at the time of the transaction request. Transaction program 130 utilizes the one or more radio wave signal devices of POS device 115 to monitor devices geographically near POS device 115. The radio wave signals may be, for example, Wi-Fi®, Bluetooth®, Bluetooth® Low Energy, (NFC), or any other wirelessly transmitted signal capable of transmitting data capable of identifying user device(s) 125-1 through 125-N. Transaction program 130 may identify user devices 125 by, for example, MAC address of the particular user device 125. In some embodiments, transaction program 130 continuously, or periodically scans for nearby user devices 125. In some embodiments, transaction program 130 utilizes a threshold to determine monitored user devices 125 within a period of time of the transaction. For example, an administrative user may set a time threshold to one minute, indicating that any devices identified in the minute before the transaction was initiated should be considered as monitored user devices 125 at the time of the transaction request. User devices 125 may be devices of the user performing the transaction or, alternatively, may also be other users in the general vicinity of POS device 115, so long as the user devices 125 are within range of the radio wave signal device(s) of POS device 115.

In step 230, transaction program 130 processes the requested transaction and sends transaction details and monitored user device 125 information to financial institution server 140 or another financial institution server associated with processing the request. In general, transaction program 130 approves/denies the transaction based on the credit/debit card information (e.g., routing numbers, account numbers, the identity of the owner of the credit card), other type of payment information, and whether authorization has been granted (if necessary). In some embodiments, authorization is granted by a security layer associated with the card/account by comparing service set identifier (SSID) information associated with the retail establishment Wi-Fi® to verify the origin of the purchase being at the retail establishment. Transaction program 130 collects transaction details, such as the card/account details, date, time, amount, goods/services transferred, location, and other information. Transaction program 130 stores the transaction details along with the identified monitored devices at the time of the transaction, and, in some embodiments, store Wi-Fi® information (e.g., SSID). The result is transaction data that may include transaction information, card/account information, monitored nearby user device 125 information, and store Wi-Fi® information. Transaction program 130 sends the transaction data to financial institution server 140 to be stored to transaction data 140. In some embodiments, transaction program 130 causes the transaction data to be stored to transaction data 140 in a secure and encrypted manner.

Figure 3:
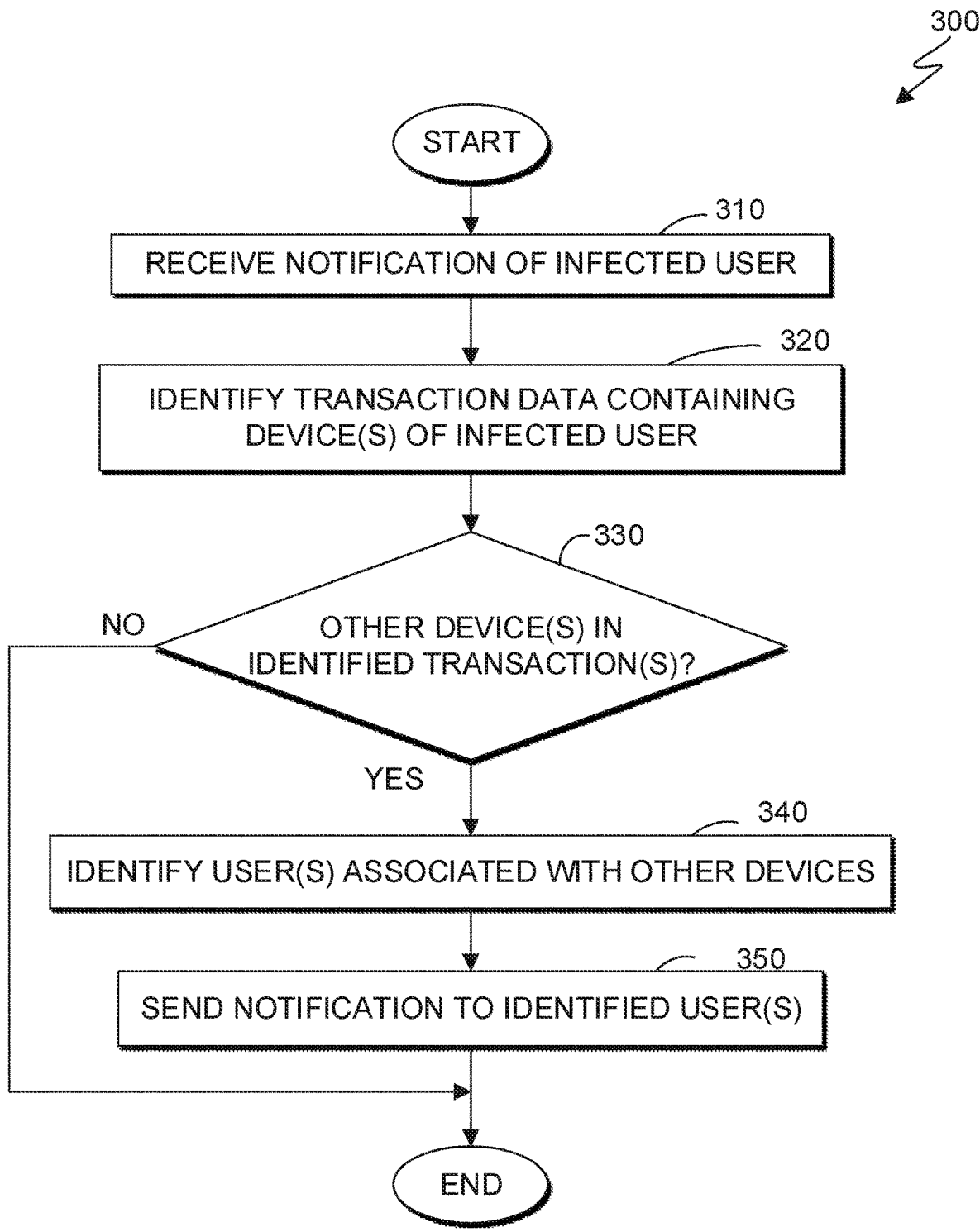
FIG. 3 is a flowchart depicting operation steps of a contact tracing program executing within the computer environment of FIG. 1, for identifying and notifying users that may have been exposed to a user infected with an infectious disease based on device information obtained from transaction data, in accordance with an embodiment of the present invention.

FIG. 3 depicts a flowchart 300 for the steps of contact tracing program 145, executing within computing environment 100 of FIG. 1, for performing contact tracing steps to identify individuals that may have been exposed to an infectious disease by identifying devices that were located geographically near a known infected individual at a time of processing a transaction, in accordance with an embodiment of the present invention. It should be recognized that, while the steps of contact tracing program 145 described herein are performed by a financial instruction server, such as financial institution server 110, other embodiments are contemplated in which another entity server, such as contact tracing server 120, is instead given access to necessary information associated with the transactions and upon receiving the necessary information, analyzes the information and sends out any necessary notifications to possibly infected user.

In one embodiment, initially, a user identifies that they have tested positive or otherwise been inflicted with an infectious disease or, in certain circumstances, has been deemed at high risk of being inflicted with an infectious disease. Such a user may contact a public healthy entity or entity that provides contact tracing services in order to prevent spread of infectious diseases, and the user may correspond with such an entity so that the entity is aware of any needed details surrounding the user's infection. In some embodiments, a user uses a device, such as a user device 125 to contact a contact tracing entity via contact tracing server 120 and may, for example utilize an application GUI to cause relevant information to be stored to contact tracing server. Such relevant information may include data about the user (e.g., name, birthday, address, demographic information, contact information), data about the infection (e.g., date tested positive, type of infectious disease, symptoms), and/or user device information, such as user device(s) 125-1.

In step 310, contact tracing program 145 receives a notification of an infected user. Contact tracing program 145 may receive the notification of the infected user from contact tracing server 120 as a result of the infected user providing information to contact tracing server 120 such that contact tracing services may be provided. In some embodiments, the notification is device information associated with the user, such as the device information used to identify user device(s) 125-1 through 125-N. In other embodiments, the notification is an identity of the user, such as a user's name. The notification may also include a time period specifying when close contact users may be at risk of infection due to exposure to the infected user. Such a time period may be determined as a result of the contact tracing services provided by contact tracing server 120 and may vary based on the type of infectious disease, symptoms experienced by the infected user, date testing positive for the infectious disease, or a variety of other factors. The notification may also include a message or template that should be used in any notifications sent to potentially exposed individuals. For example, the message may include the type of infectious disease the individual may have been exposed to, any symptoms they may experience, recommendations for treatment/testing, instructions to quarantine, contact information to obtain additional information, or any other information. If a template is provided, the template may have a field that is to be filled in with the date/time/location of the potential exposure as well as a field for the exposed user's device information that lead to the determination that the user was exposed. Accordingly, a potentially exposed user may be able to use the information to determine whether they were actually exposed to the infectious disease or, for example, if they had instead let another borrow their device.

In step 320, contact tracing program 145 identifies transactions stored to transaction data 140 that contain device information for user device(s) 125 of the infected user. As an example and for discussion purposes only, user device(s) 125-1 are the infected user's devices. Accordingly, if contact tracing program 145 was provided with unique identifying information of the devices with the notification of the infected user, contact tracing program 145 searches transaction data 140 for occurrences of the provided device information within transactions stored to transaction data 140. If contact tracing program 145 is provided with a name of the user, or other means to identify the user, contact tracing program 145 may access device data 135 to identify known devices that have been linked to the user's account. Then, contact tracing program 145 may similarly use the extracted device information to search for individual transactions, from transaction data 140, that include device information from user device(s) 125-1 of the infected user. In some embodiments, contact tracing program 145 only searches transactions that occurred within a particular date range, such as a date range specified by a time period of the notification. In some embodiments, if contact tracing program 145 is provided with the name of the infected user, contact tracing program 145 may also search transactions involving the user that did not include a user device of the user, such as user device(s) 125-1. For example, the user may perform a transaction using a credit card and the user may not be in possession of user device(s) 125-1 at the time of the transaction. However, other user device(s) 125-2 through 125-N can still be identified by contact tracing program 145. Therefore, even though no user device(s) 125-1 for the infected user are a part of the transaction, there may be other user device(s) 125 that cause the transaction to remain relevant for analysis by contact tracing program 145.

In decision 330, contact tracing program 145 determines whether other user device(s) 125 (i.e., other than user device(s) 125-1) are included within any of the identified transactions. Contact tracing program 145 searches the identified transactions for other user device information, such as MAC address information associated with user device(s) 125-2 through 125-N. As previously described, each transaction also includes device information obtained wirelessly by POS device 115 for devices geographically near POS device 115 at the time of the transaction. Accordingly, contact tracing program 145 accesses the data from each identified transaction and searches for the presence of other devices (e.g., user device(s) 125-1 through 125-N) based on the stored device information.

If contact tracing program 145 determines that the only device geographically near POS device 115 during the identified transaction(s) were user devices of the infected user (e.g., user device(s) 125-1) (decision 330, no branch), no close contact users are identified and the process is complete.

If contact tracing program 145 determines that there are other devices (e.g., user device(s) 125-2 through 125-N) listed in the identified transaction(s) (decision 330, yes branch), contact tracing program identifies user(s) associated with the other devices (step 340). Contact tracing program 145 may identify the user(s) associated with the other devices by comparing the identified user device information (e.g., MAC address) to device information stored to device data 135. As described above, users may voluntarily store device information for a variety of reasons, such as multi-factor authentication, verification, or other purposes. Contact tracing program 145 can therefore identify the other users from the stored device information that is associated with the user account. In some embodiments, a user may not store device information to device data 135 and contact tracing program 145 may not be able to identify the user by comparing the device information to device data 135. For example, the user may not have an account with the financial institution that manages financial institution server 110. If contact tracing program 145 is unable to determine the other users, contact tracing program 145 may, alternatively, send the device information (e.g., MAC address) corresponding to the unidentified user(s) to contact tracing server 120. Contact tracing server 120 may then be able to query other entities to possibly identify the user. For example, contact tracing server may query other financial institutions, device manufacturers (e.g., smartphone manufacturers), internet service providers (ISPs), cellular service providers, or other entities that may be able to determine the identity of a user from the corresponding device information. It should be noted that, upon storing device information capable of identifying a user, the user is able to adjust privacy settings, opt in, or opt out to any types of the sharing of their identifying data that is described herein. Further, even in embodiments where information is sent to contact tracing server 120, device information may be the only sent information, resulting in security anonymity with respect to the identity of the actual user.

In step 350, contact tracing program 145 sends a notification to the identified user(s) associated with the other device(s). In some embodiments, the content of the notification is based on a message or template provided by contact tracing server 120. In other embodiments, contact tracing program 145 sends relevant information to contact tracing server 120 and a program of contact tracing server 120 actually sends the notification to the identified user(s). Generally, contact tracing program 145 sends a notification to each of the identified user(s) that includes information specifying that the respective identified user was exposed to an individual who has an infectious disease and that they may have been exposed as well. Particular contents of the message may vary but may include information such as date/time/location of the exposure, the user device(s) of the user that connect the user to the potential exposure, the particular infectious disease the user was potentially exposed to, information about the particular infectious disease, possible symptoms the user may experience, contact information for the user to obtain additional information, recommendations or legal requirements relating to testing, quarantining, and obtaining medical treatment, or any other information that may be relevant to aid in contact tracing and slowing/preventing the spread of an infectious disease.

Figure 4:
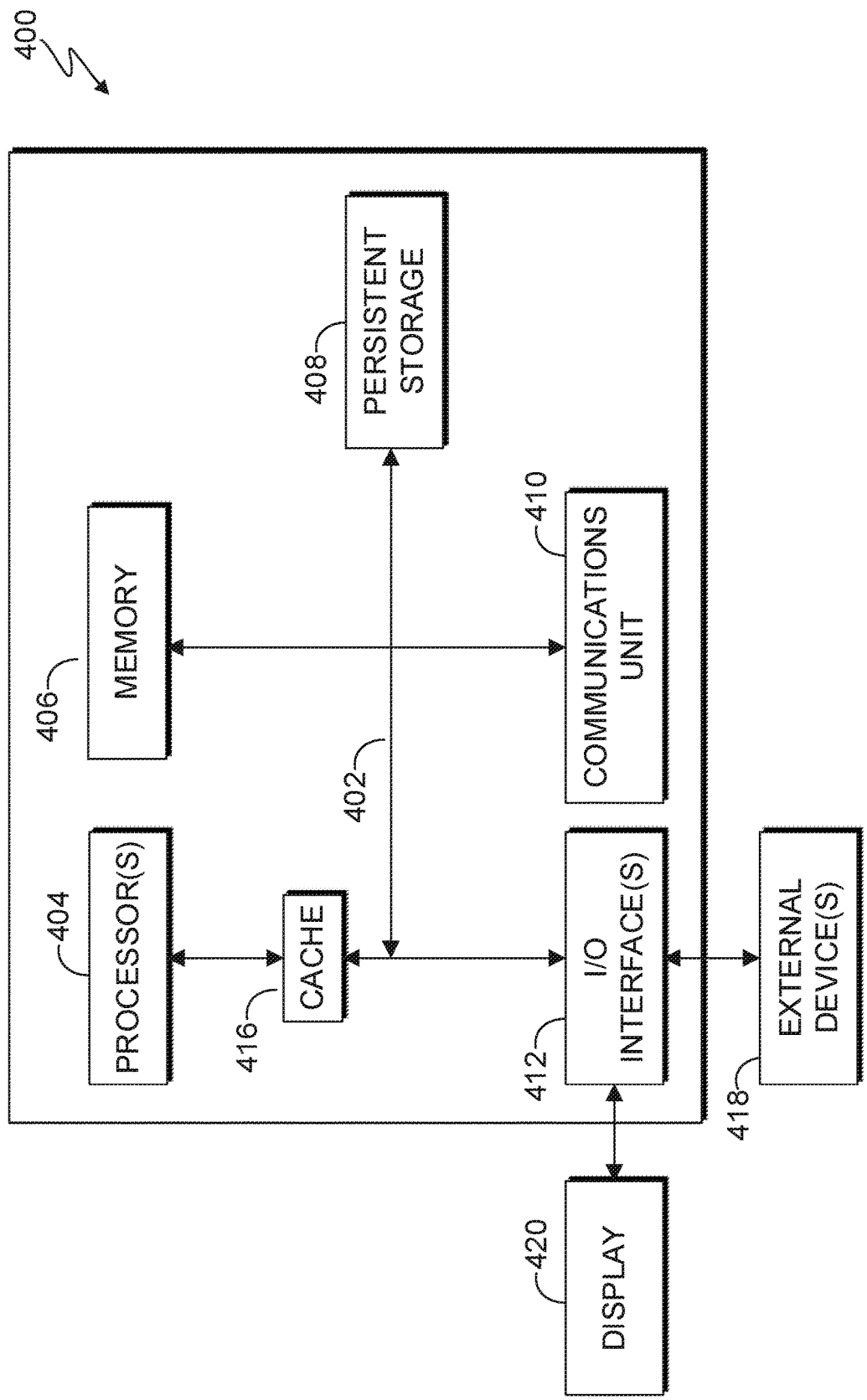
FIG. 4 is a block diagram of components of the proxy server computer executing the intelligent mapping program, in accordance with an embodiment of the present invention.

FIG. 4 depicts a block diagram 400 of components of financial institution server 110, POS device 115, contact tracing server 120, and user device(s) 125-1 through 125-N, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Financial institution server 110, POS device 115, contact tracing server 120, and user device(s) 125-1 through 125-N each include communications fabric 402, which provides communications between cache 416, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 406 and persistent storage 408 are computer readable storage media. In this embodiment, memory 406 includes random access memory (RAM). In general, memory 406 can include any suitable volatile or non-volatile computer readable storage media. Cache 416 is a fast memory that enhances the performance of computer processor(s) 404 by holding recently accessed data, and data near accessed data, from memory 406.

Device data 135, transaction data 140, and contact tracing program 145 may be stored in persistent storage 408 of financial institution server 110 and in memory 406 of financial institution server 140 for execution and/or access by one or more of the respective computer processors 404 of financial institution server 110 via cache 416 of financial institution server 110. Transaction program 130 may be stored in persistent storage 408 of POS device 115 and in memory 406 of POS device 115 for execution by one or more of the respective computer processors 404 of POS device 115 via cache 416 of POS device 115. In an embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices. In these examples, communications unit 410 includes one or more network interface cards. Communications unit 410 may provide communications through the use of either or both physical and wireless communications links. Device data 135, transaction data 140, and contact tracing program 145 may be downloaded to persistent storage 408 of financial institution server 110 through communications unit 410 of financial institution server 110. Transaction program 130 may be downloaded to persistent storage 408 of POS device 115 through communications unit 410 of POS device 115.

I/O interface(s) 412 allows for input and output of data with other devices that may be connected to server computer 102. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., transaction program 130, device data 135, transaction data 140, and contact tracing program 145, can be stored on such portable computer readable storage media and can be loaded onto the respective persistent storage 408 via respective I/O interface(s) 412. I/O interface(s) 412 also connect to a display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
    receiving, by one or more processors, point-of-sale (POS) purchase data from a cash register that includes a radio wave signal device, wherein:
        the POS purchase data comprises: (i) details of a POS purchase by a first user, including a location of the first user, and (ii) a media access control (MAC) address corresponding to a first device of a second user which: (i) is not a device used to perform the POS purchase and (ii) is not associated with the first user; and
        the MAC address of the first device is captured by the radio wave signal device of the cash register utilizing wireless communication to scan for devices within a threshold distance of the cash register within a threshold period of time of the POS purchase;
    storing, by one or more processors, the POS purchase data to a repository on a server;
    receiving, by one or more processors, notification that the first user is an infected user;
    determining, by one or more processors, that the first user made the POS purchase;
    retrieving, by one or more processors, the POS purchase data from the repository;
    identifying, by one or more processors, the first device from the retrieved POS purchase data;
    determining, by one or more processors, the second user based on comparing the MAC address of the first device to stored information which identifies the first device as belonging to the second user; and
    sending, by one or more processors, a notification to the second user.

2. The computer-implemented method of claim 1, wherein the wireless communication is of a type selected from the group consisting of: Wi-Fi, Bluetooth, Bluetooth Low Energy, and near-field communication (NFC).

3. The computer-implemented method of claim 1, wherein determining that the first user made the POS purchase comprises identifying, by one or more processors, a device of the infected user from the MAC address of the POS purchase data.

4. The computer-implemented method of claim 1, wherein the received notification of the infected user further includes a time period, further comprising:
    determining, by one or more processors, that the POS purchase was processed within the time period.

5. The computer-implemented method of claim 1, wherein identifying the first device from the POS purchase data comprises identifying that the MAC address corresponding to the first device is associated with an account of the second user.

6. A computer program product comprising:
one or more computer readable storage media, and program instructions collectively stored on the one or more computer readable storage media, the program instructions comprising:
program instructions to receive point-of-sale (POS) purchase data from a cash register that includes a radio wave signal device, wherein:
the POS purchase data comprises: (i) details of a POS purchase by a first user, including a location of the first user, and (ii) a media access control (MAC) address corresponding to a first device of a second user which: (i) is not a device used to perform the POS purchase and (ii) is not associated with the first user; and
the MAC address of the first device is captured by the radio wave signal device of the cash register utilizing wireless communication to scan for devices within a threshold distance of the cash register within a threshold period of a time of the POS purchase;
program instructions to store the POS purchase data to a repository on a server;
program instructions to receive notification that the first user is an infected user;
program instructions to determine that the first user made the POS purchase;
program instructions to retrieve the POS purchase data from the repository;
program instructions to identify the first device from the POS purchase data;
program instructions to determine the second user based on comparing the MAC address of the first address of the first device to stored information which identifies the first device as belonging to the second user; and
program instructions to send a notification to the second user.

7. The computer program product of claim 6, wherein the wireless communication is of a type selected from the group consisting of: Wi-Fi, Bluetooth, Bluetooth Low Energy, and near-field communication (NFC).

8. The computer program product of claim 6, wherein determining that the first user made the POS purchase comprises program instructions to identify a device of the infected user from the MAC address of the POS purchase data.

9. The computer program product of claim 6, wherein the received notification of the infected user further includes a time period, further comprising:
program instructions, collectively stored on the one or more computer readable storage media, to determine that the POS purchase was processed within the time period.

10. The computer program product of claim 6, wherein program instructions to identify the first device from the POS purchase data comprise program instructions to identify that the MAC address corresponding to the first device is associated with an account of the second user.

11. A computer system comprising:
one or more computer processors, one or more computer readable storage media, and program instructions collectively stored on the one or more computer readable storage media for execution by at least one of the one or more computer processors, the program instructions comprising:
program instructions to receive point-of-sale (POS) purchase data from a cash register that includes a radio wave signal device, wherein:
the POS purchase data comprises: (i) details of a POS purchase by a first user, including a location of the first user, and (ii) a media access control (MAC) address corresponding to a first device of a second user which: (i) is not a device used to perform the POS purchase and (ii) is not associated with the first user; and
the MAC address of the first device is captured by the radio wave signal device of the cash register utilizing wireless communication to scan for devices within a threshold distance of the cash register within a threshold period of a time of the POS purchase;
program instructions to store the POS purchase data to a repository on a server;
program instructions to receive notification that the first user is an infected user;
program instructions to determine that the first user made the POS purchase;
program instructions to retrieve the POS purchase data from the repository;
program instructions to identify the first device from the POS purchase data;
program instructions to determine the second user based on comparing the MAC address of the first address of the first device to stored information which identifies the first device as belonging to the second user; and
program instructions to send a notification to the second user.

12. The computer system of claim 11, wherein the wireless communication is of a type selected from the group consisting of: Wi-Fi, Bluetooth, Bluetooth Low Energy, and near-field communication (NFC).

13. The computer system of claim 11, wherein determining that the first user made the POS purchase comprises program instructions to identify a device of the infected user from the MAC address of the POS purchase data.

14. The computer system of claim 11, wherein the received notification of the infected user further includes a time period, further comprising:
program instructions, collectively stored on the one or more computer readable storage media, to determine that the POS purchase was processed within the time period.

15. The computer system of claim 11, wherein program instructions to identify the first device from the POS purchase data comprise program instructions to identify that the MAC address corresponding to the first device is associated with an account of the second user.

* * * * *